(12) United States Patent
Vann

(10) Patent No.: US 8,028,591 B2
(45) Date of Patent: Oct. 4, 2011

(54) SYSTEM AND METHOD FOR SELECTIVE RETRIEVAL OF SUPPORT BEADS

(75) Inventor: Charles S. Vann, El Granada, CA (US)

(73) Assignee: Applied Biosystems LLC, Carlsbad, CA (US)

( * ) Notice: Subject to any disclaimer, the term of this patent is extended or adjusted under 35 U.S.C. 154(b) by 1090 days.

(21) Appl. No.: 11/747,667

(22) Filed: May 11, 2007

(65) Prior Publication Data

US 2008/0281466 A1    Nov. 13, 2008

(51) Int. Cl.
*B01L 3/00* (2006.01)
*G01N 1/00* (2006.01)
(52) U.S. Cl. ..... 73/864.16; 73/864; 700/214; 536/25.41
(58) Field of Classification Search ............ 422/99, 422/63, 65, 100, 102; 222/402.1, 566; 700/245, 700/214, 213; 73/864, 864.01, 864.16; 536/25.4, 536/25.41
See application file for complete search history.

(56) References Cited

U.S. PATENT DOCUMENTS

| | | | | |
|---|---|---|---|---|
| 4,341,568 | A * | 7/1982 | Christensen | 134/21 |
| 4,937,048 | A * | 6/1990 | Sakai et al. | 422/63 |
| 6,074,609 | A * | 6/2000 | Gavin et al. | 422/99 |
| 6,471,917 | B1 * | 10/2002 | Velkovska et al. | 422/100 |
| 7,118,892 | B2 | 10/2006 | Ammann et al. | |
| 7,361,309 | B2 * | 4/2008 | Vann et al. | 422/99 |
| 7,615,193 | B2 * | 11/2009 | Vann et al. | 422/100 |
| 7,799,279 | B2 * | 9/2010 | Fulton et al. | 422/425 |
| 2006/0013984 | A1 * | 1/2006 | Sandell et al. | 428/40.1 |
| 2006/0063159 | A1 * | 3/2006 | Vann | 435/6 |
| 2006/0210434 | A1 | 9/2006 | Vann et al. | |
| 2006/0228734 | A1 * | 10/2006 | Vann et al. | 435/6 |
| 2007/0116600 | A1 * | 5/2007 | Kochar et al. | 422/65 |
| 2009/0025489 | A1 * | 1/2009 | Christensen et al. | 73/864 |

OTHER PUBLICATIONS

International Search Report and the Written Opinion of the International Searching Authority dated Oct. 22, 2008.

* cited by examiner

*Primary Examiner* — Ronnie Mancho

(57) ABSTRACT

Systems and methods are provided that can include a storage and retrieval robot operating under program control to extract a selective number of support beads from a storage or retainment region, for dispensing to titer wells or other vessels for assays and other purposes. According to various embodiments, the storage and retrieval robot can position a capture device over any one or more storage wells containing oligonucleotide or other material support beads, and withdraw or extract those support beads into a collection tube under vacuum pressure or other force. According to various embodiments, a selected number of support beads can be extracted, using a linear motor piston to limit available space for support bead insertion. According to various embodiments, the collected support beads can be dispensed into one or more destination tubes, wells, or other containers, surfaces, vessels, receptacles or mixture containment region, for use in assays or other purposes. According to various embodiments, a calculated plurality of support beads can be extracted or mixed in selective quantities. According to various embodiments, a sample subset of the supply support beads can be taken, to calculate an amount of actual oligonucleotide contained in the support beads. According to various embodiments, an adjustment or normalization of the number of support beads dispensed can be performed to compensate for variations in oligonucleotide amount, thereby enhancing the uniformity of concentration in solution.

21 Claims, 3 Drawing Sheets

SYSTEM AND METHOD FOR SELECTIVE RETRIEVAL OF SUPPORT BEADS

FIELD

The present teachings relate to a system and method for selective retrieval of beads, such as support beads comprising oligonucleotides or other materials, that can be selectively extracted from storage wells or supports, and dispensed into tubes or other receptacles.

BACKGROUND

Various, chemical, biological, and other substances or materials can be incorporated into beads. If collections of such beads can be stored and retrieved with an automated or robotic handling system, customers wishing to obtain those beads can receive the bead types they want from inventory at reasonable cost, and in a potentially short delivery time. Previous bead handling systems stored inventory beads in multiple capsules, one for each bead type, with each capsule containing a pre-loaded number of beads. If the beads were subsequently dispensed into titer plates or trays, for example at a rate of one bead per well, then the number of beads per capsule would dictate a minimum number of plates or lot size that the customer would be required to purchase. Some customers, however, may only wish to purchase one plate while others may desire hundreds or more. Establishing a minimum plate purchase can force some customers to buy more plates than they need, inefficiently raising the cost. In addition, when inventory beads are stored in capsule format, the number of beads contained in a capsule can be less than some ordered quantities, requiring multiple capsule retrievals to extract the necessary beads and fill the order, increasing retrieval time and cost. In addition, when beads are dispensed to a plate at a rate of one bead per well or multiple beads per well, the concentration of the oligonucleotide or other materials embedded in the beads can vary, leading to differences in oligonucleotide concentrations when the beads are used. Other problems in existing bead handling and dispensing systems exist.

SUMMARY

The present teachings provide systems and methods for selective retrieval of a variable quantity of support beads from storage, overcoming these and other problems in the art. According to various embodiments of the present teachings, a robotic bead collector and release assembly can be driven with positioning motors to move a collection or capture device over wells or other retainment regions storing various oligonucleotide or other support beads. According to various embodiments, one, two, three, or other numbers of support beads may be extracted from selected retainment regions, and dispensed into a receiving tube, titer plate, or other receptacle or destination. According to various embodiments, the bead collector and release assembly can be programmed to extract different support bead types from different storage wells, and to dispense or mix those support beads and their constituent materials in desired quantities.

According to various embodiments, the extraction of desired bead material need not be limited to one support bead at a time. According to various embodiments, the oligonucleotide or other concentrations of support beads on one or more storage wells can be sampled and measured, to determine a baseline concentration. According to various embodiments, the baseline concentration can be used to adjust the amount or number of support beads dispensed, to achieve a more uniform concentration, for example, when the support beads are melted during thermal cycling or cleaved in solution.

BRIEF DESCRIPTION OF THE DRAWINGS

Various embodiments of the present teachings are exemplified in the accompanying drawings. The present teachings are not limited to the embodiments depicted in the drawings, and include equivalent structures and methods as set forth in the following description and as will be know to those of ordinary skill in the art in view of the present teachings. In the drawings.

DESCRIPTION OF VARIOUS EMBODIMENTS

Figure 1:
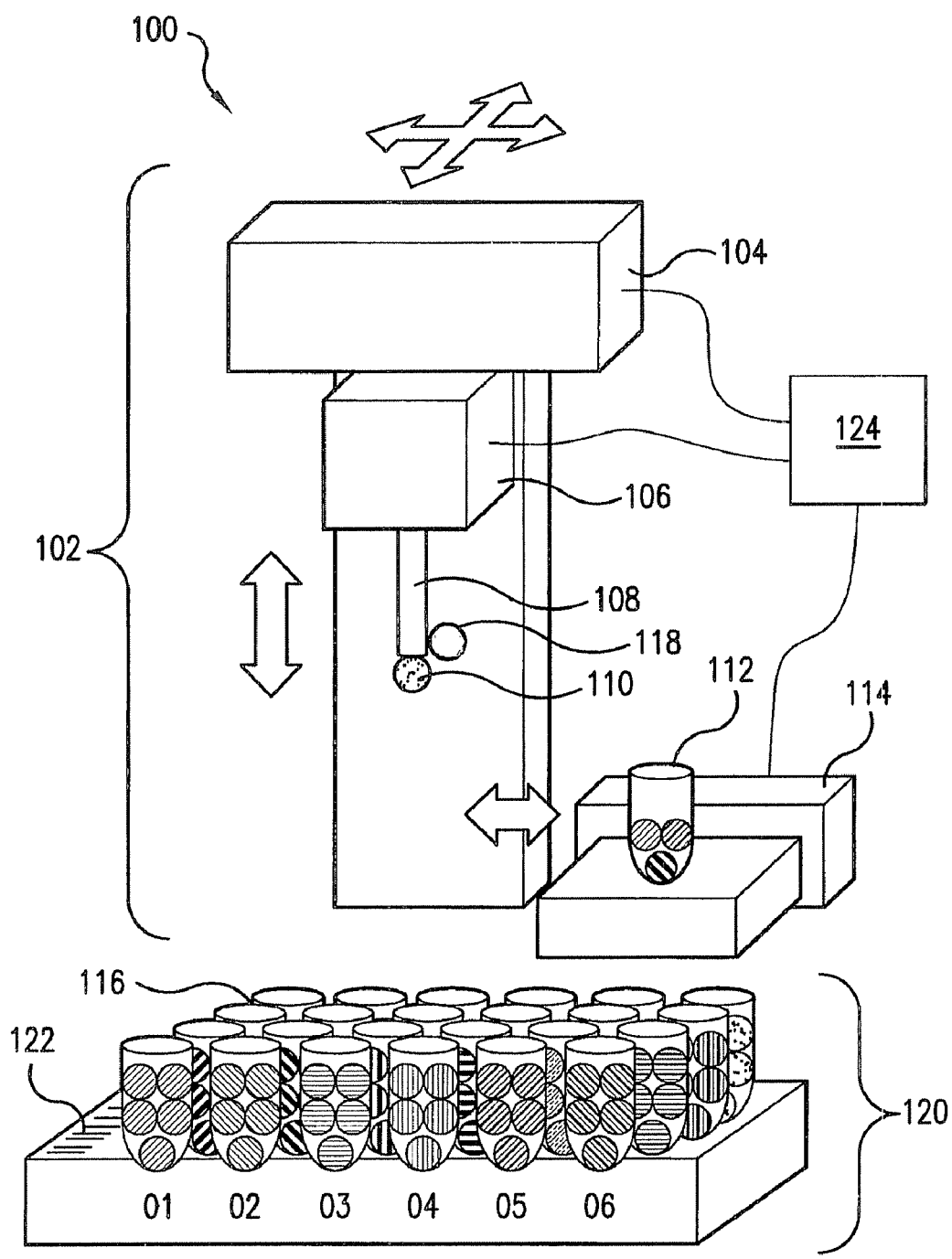
FIG. 1 is a schematic illustration of a handling system including an illustration of ranges of motions and motion directions that a handling system according to various embodiments of the present teachings can perform with respect to a plurality of retainment regions.

According to various embodiments, a system is provided that can comprise a plurality of storage wells or retainment regions, a mixture retainment region, a handling device, a control unit, and other components cooperating to retrieve and dispense selective quantities of supports or beads, herein, also referred to as support beads. Each of the retainment regions can be adapted to retain a respective type of support bead, for example comprising chemical, biological, or other material supported by, contained in, or otherwise attached to, a support, particle, bead, flake, or other surface-bearing structure, herein referred to as a support bead. The support beads described herein need not be spherical or round but in some embodiments they are nearly or perfectly spherical, that is, substantially spherical. The control unit can be programmed, programmable, and/or operable, to control the handling device to extract and pool in the mixture retainment region different support beads from different ones of the retainment regions, to form a pool or mixture in the mixture retainment region.

According to various embodiments of the present teachings, the support beads that are stored, retrieved, and dispensed can comprise oligonucleotides thereon and/or therein. According to the various embodiments, the oligonucleotides can comprise an amino acid molecule, for example, a peptide, a nucleotide, a polynucleotide, a 10-mer nucleotide, a 20-mer nucleotide, or other oligonucleotide, or another substance or material. According to various embodiments a calculated plurality of support beads can be retrieved and dispensed, and in the amount or quantity of the plurality can be determined based on a concentration of one or more reagents captured or otherwise supported by the support beads. In some embodiments, a capture device can be provided that can individually handle a single support bead having a spherical shape and a diameter of from about 10 microns to about 2000 microns, for example, from about 20 microns to about 500 microns, or from about 30 microns to about 100 microns. In some embodiments, a capture device can be provided that can individually handle a single support bead having other than a spherical shape and at least one minimum dimension of from about 10 microns to about 2000 microns, for example, from about 20 microns to about 500 microns, or from about 30 microns to about 100 microns.

In some embodiments, the capture device can comprise at least one linear motor, and/or a robot. In some embodiments, the at least one capture device can comprise a plurality of capture devices and in some embodiments each can comprise its own linear motor and/or robot. Each capture device can comprise at least one sensor for sensing a type of support bead and/or its location.

According to various embodiments, at least one mixture retainment region can be provided into which extracted support beads can be dispensed. In some embodiments, the at least one mixture retainment region can comprise a plurality of mixture retainment regions. One or more of the mixture retainment regions and/or plurality of retainment regions can comprise a removable container, and in some embodiments, at least the plurality of retainment regions can comprise a plurality of individually removable containers. Each container can be respectively tagged.

According to various embodiments illustrated in FIG. 1, a storage and retrieval robot 100 can operate to extract support beads comprising supported oligonucleotides, or other material stored therein or thereon, from an addressable array 120 comprising multiple retainment regions 116, such as tubes, wells, or other vessels, container, surface, or receptacle. As illustrated in FIG. 1, addressable array 120 can comprise one or more retainment regions 116 arranged in a rectangular grid or array. According to various embodiments, the one or more retainment regions 116 can be arranged in other patterns or configurations. According to various embodiments, the addressable array 120 from which the oligonucleotide support beads or other supports are extracted can be identified by a readable identifier 122, such as, for example a barcode, an electronic memory, a transponder element such as an RFID device, or other optical, non-optical, electronic, or otherwise readable media and/or tag.

According to various embodiments as illustrated in FIG. 1, the storage and retrieval robot 100 can include a set of linear motors 104, 106, and 114 arranged to drive extraction and dispensing elements over a source retainment region 116 or regions, and to convey extracted support beads to a mixture retainment region 112, such as a receiving tube, well, or other vessel, container, surface, or receptacle. According to various embodiments as illustrated, linear motor 104 can comprise a horizontally moveable motor configured to selectively move in a horizontal plane. According to various embodiments as illustrated, linear motor 106 can comprise a vertical motor cooperating with linear motor 104 to cause capture device 108 to descend or lift in a vertical direction, so as to position capture device 108 come into a position in close proximity to one or more retainment region 116 of addressable array 120. According to embodiments as illustrated, the storage and retrieval robot 100 can also comprise a linear motor 114 configured to move mixture retainment region 112, such as a tube, well, or other vessel, container, surface, or receptacle, in a horizontal plane to receive an extracted support.

According to various embodiments as illustrated, storage and retrieval robot 100 can also comprise a sensor 118 disposed proximate a distal tip of capture device 108. According to various embodiments, sensor 118 can comprise an optical, thermal, electromagnetic, or other sensor or detector to detect, for example, the position, presence, type, temperature, weight, optical emission, or other parameters of extracted supports, for example, support beads residing in or being conveyed to one or more retainment region 116 or mixture containment region 112, or other materials or objects. According to various embodiments, the storage and retrieval robot 100 can operate under control of control unit 124. According to various embodiments, control unit 124 can comprise, for example, a processor or microcontroller operating Linder programmed control, for example, to direct the motion of linear motors 104, 106, and 114 and control other operations of the storage and retrieval robot 100.

Figure 2A:
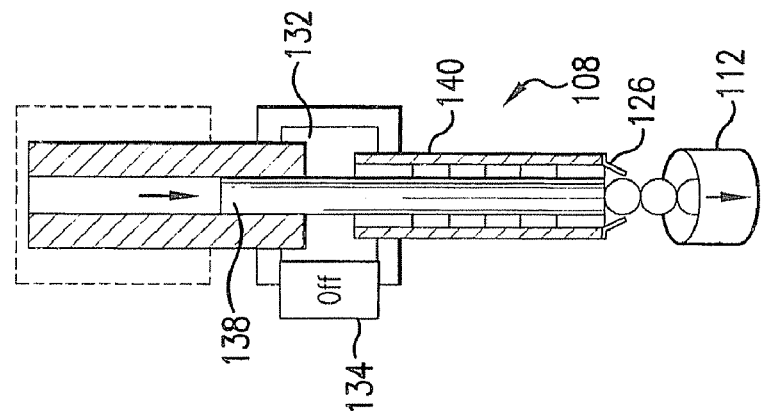
FIGS. 2(A)-2(E) illustrate various aspects of a capture device and associated elements that can be used to extract support beads from wells or retainment regions, according to various embodiments.

Extraction and delivery of selected support beads is illustrated by the manipulation of support beads shown in the various embodiments of FIGS. 2(A)-2(D). According to embodiments as shown, capture device 108 can comprise an elongated tube 140 having an elliptical bore 130 formed therein. Tube 140 can comprise a distal end having an opening with a cross-septum membrane 126, for example, a set of slitted flexible rubber flaps, or other membrane or material. According to embodiments as illustrated in FIG. 2(A), capture device 108 can comprise a linear motor piston 138 communicating with a vacuum chamber 132 and elliptical bore 130. A vacuum motor 134 can be connected to vacuum chamber 132 to evacuate air from vacuum chamber 132.

Figure 2B:
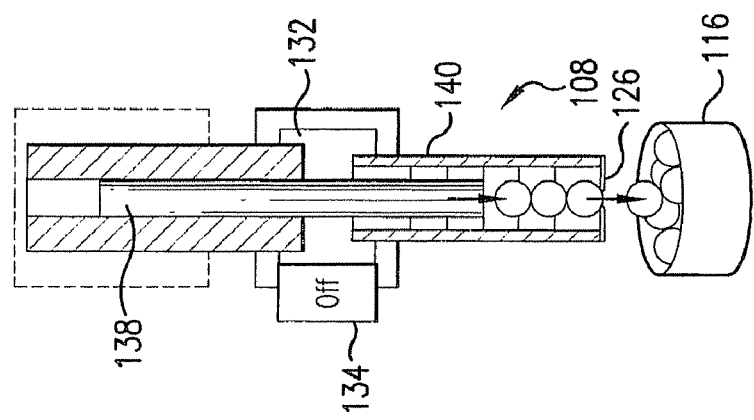

As illustrated in FIG. 2(B), according to various embodiments, elliptical bore 130 can be sized to receive a predetermined number of support beads from the retainment region 116 drawn into elliptical bore 130 through cross-septum membrane 126. As illustrated in FIG. 2(B), according to various embodiments, linear motor piston 138 can be driven to a predetermined position in elliptical bore 130 so as to act as a stop such that elliptical bore 130 can receive a desired number of support beads from retainment region 116. According to various embodiments, the support beads stored in retainment region 116 can be drawn through cross-septum membrane 126 and into elliptical bore 130 by an airflow in a vertical or other direction caused when vacuum motor 134 evacuates vacuum chamber 132, causing an extraction or suction force in an upward direction. According to embodiments as shown, the support beads drawn from retainment region 116 do not block the air passageway of tube 140 due to, in various embodiments, the elliptical cross-sectional shape of elliptical bore 130, which provides a margin of clearance around spherical or approximately spherical support beads drawn into elliptical bore 130. According to embodiments as shown, only a desired number of support beads, illustratively three, are drawn into elliptical bore 130 of capture device 108, due to the positioning of linear motor piston 138. It will be appreciated that other numbers of support beads can be extracted and/or dispensed as programmed and/or desired.

Figure 2C:
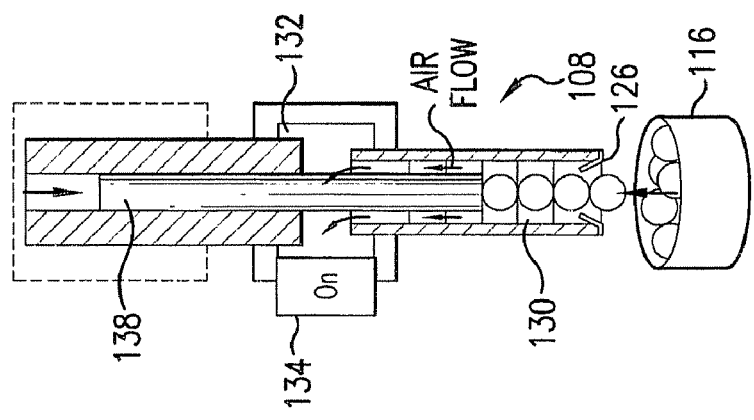

As illustrated in FIG. 2(C), according to various embodiments, after a desired number of support beads have been extracted from retainment region 116 into tube 140 of capture device 108, the number of support beads being determined by linear motor piston 138 acting as an axial limiter or stop, vacuum motor 134 can be turned off, relieving the vacuum in vacuum chamber 132. In the absence of a vertical air flow due to vacuum drawn by vacuum motor 134, any residual support bead, or other particle or object, pinned against cross-septum membrane 126 by vacuum air flow can drop back into retainment region 116. Cross-septum membrane 126 can, according to embodiments, have rubber flaps or other membranes or surfaces having sufficient rigidity to retain the desired number of support beads in the elliptical bore 130 after vacuum motor 134 has been turned off, and any residual support beads have dropped back into retainment region 116.

Figure 2D:
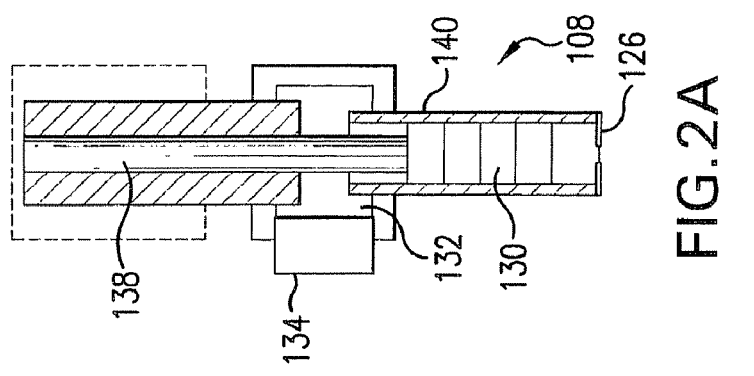
Figure 2E:
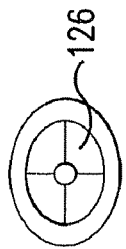

According to various embodiments illustrated in FIG. 2(D), after the desired number of support beads have been secured in capture device 108 and vacuum motor 134 has been turned off, capture device 108 can, in various embodiments, eject the selected set of retrieved support beads by activating linear motor piston 138. As shown in FIG. 2(D), linear motor piston 138 can be driven to a downward position, forcing the collected support beads located in tube 140 to be ejected or displaced through the cross-septum membrane and be dispensed from the capture device 108. According to various embodiments, the set of collected support beads can be dispensed or expelled into mixture retainment region 112, such as a tube, well, or other vessel, container, surface, or receptacle, under the mechanical driving force supplied by linear motor piston 138. After the last collected support bead is dispensed, cross-septum membrane 126 can return to an unbiased, closed position at the mouth of tube 140, and additional support bead uptake can begin if desired.

Figure 3D:
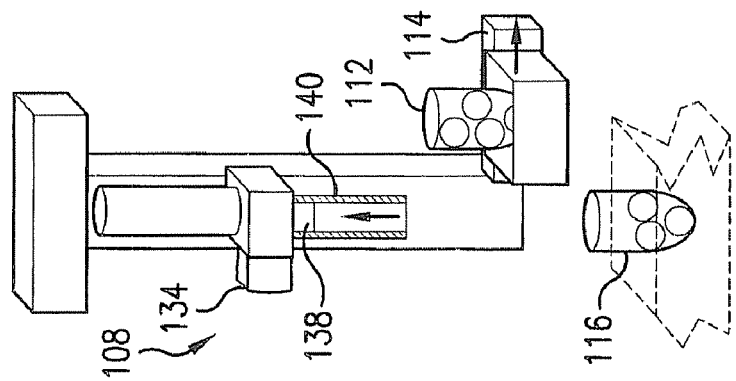
FIGS. 3(A)-3(D) illustrate a capture device and associated elements operating to dispense to expel selectively retrieved support beads into a tube or other receptacle, according to various embodiments.
Figure 3C:
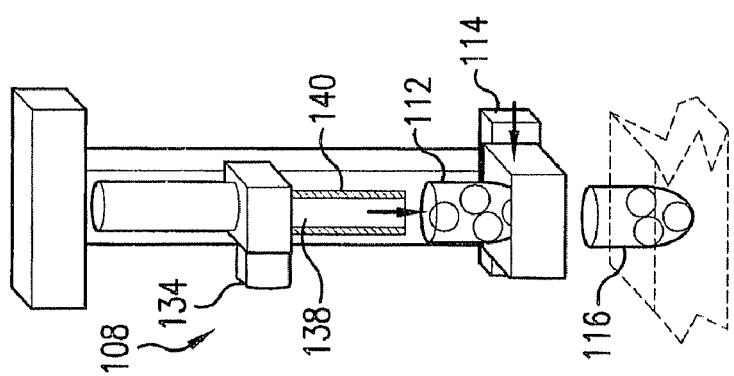
Figure 3B:
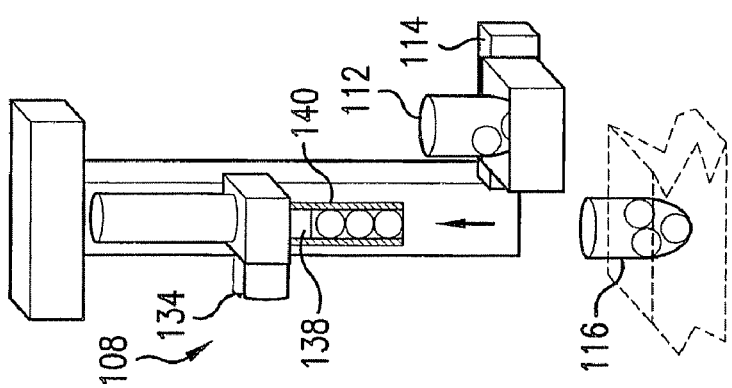
Figure 3A:
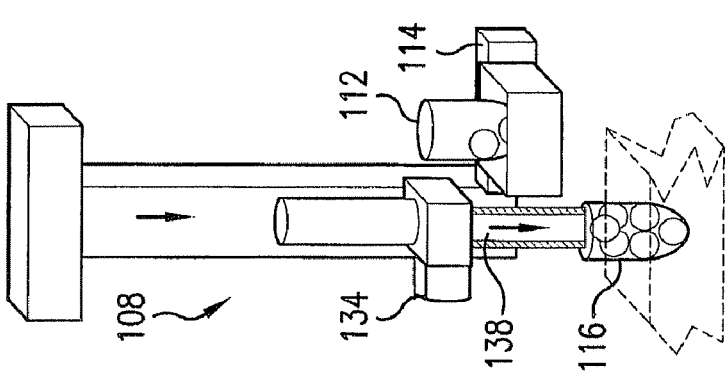

Extraction and dispensing operations exemplified according to various embodiments of the present teachings are illustrated in FIG. 3(A)-3(D). As illustrated in FIGS. 3(A) and 3(B), capture device 108 can operate to extract a desired number of support beads from a retainment region 116, such as, for example, a tube, well, or other vessel, container, surface, or receptacle, in an addressable array 120, under vacuum supplied by a vacuum motor 134, drawing a selected number of support beads into a tube 140. According to various embodiments as shown, linear motor 114 can support and movably position a mixture retainment region 112 to prepare to receive the extracted oligonucleotide or other support beads drawn into tube 140, for example under control of control unit 124. As illustrated in FIG. 3(C), linear motor 114 can position mixture retainment region 112 underneath a distal tip of tube 140 to receive the set of selected support beads dispensed from tube 140 under force supplied by a linear motor piston 138. According to various embodiments, mixture retainment region 112 can receive one type of support bead, or multiple types of support beads, drawn from one or more retainment region 116. According to various embodiments, mixture retainment region 112 can comprise a single tube, well, or other vessel, container, surface, or receptacle. According to various embodiments, mixture retainment region 112 can comprise multiple tubes, wells, or other vessels, containers, surfaces, or receptacles. According to various embodiments, when mixture retainment region 112 comprises multiple tubes, wells, or other vessels, containers, surfaces or receptacles, each tube, well, or other receiving structure or area can receive the same or a different mixture or quantity of support beads. According to various embodiments, the storage and retrieval robot 100 can dispense all support beads contained in tube 140 into one mixture retainment region 112 at one time, or, in some embodiments, can dispense the collected support beads into different retainment regions, and/or at different times.

As illustrated in FIG. 3(D), after a desired set of support beads is collected and dispensed into mixture retainment region 112, linear motor 114 can transport mixture retainment region 112 to another position, for example, to translate or deliver mixture retainment region 112 to another area on a plate, tray, or another holder or structure. According to various embodiments, once a desired number or type of support beads are loaded, mixture retainment region 112 can be sealed or otherwise separately processed, for example for delivery to a customer or other destination. According to various embodiments, linear motor piston 138 can retract in tube 140 to prepare for additional extraction operations. According to various embodiments, the oligonucleotide or other support beads extracted and delivered by storage and retrieval robot 100 need not be stored in capsules of predetermined amount, nor dispensed into wells or receptacles in only one-bead quantity. The storage and retrieval robot 100 can instead selectively retrieve, dispense, and mix any desired number, type, amount, or quantity, herein referred to herein as a plurality, of support beads from addressable array 120 under control of control unit 124. Storage and delivery difficulties as noted above with respect to previous handler systems are therefore eliminated.

According to various embodiments of the present teachings, the capability of storage and retrieval robot 100 to accurately collect a selected number of support beads permits relatively fine-grained use of the oligonucleotide or other materials, since the number of support beads determines the total amount of oligonucleotide or other material that will be available for use. That is, the ultimate oligonucleotide or other concentration resulting from use of the collected support beads is determined by the actual collected support bead number. According to various embodiments of the present teachings, in various applications it is often desirable to have nearly the same oligonucleotide concentration for each of the selected oligonucleotides, for instance in a combined or pooled assay. According to various embodiments, for example, a concentration consistency of plus or minus 10% or better can be desirable across multiple oligonucleotide materials or other materials or assays. Several different factors can cause a different amount of oligonucleotide or other material to form or remain on or in a support bead. According to various embodiments, therefore, provision is made for normalizing or adjusting the ultimate individual oligonucleotide concentration in a pool, for purposes of uniformity. According to various embodiments, if only a single support bead is collected in mixture retainment region 112, no opportunity to normalize concentration in solution is presented. When multiple support beads are used, the standard deviation per support, of oligonucleotide concentration, for example, can be compensated for by using greater than one support of each kind in a pooling operation.

In some embodiments, adjustments in pooling can comprise pooling five or more, ten or more, twenty or more, or at least 50 support beads of each type desired. In some embodiments no more than 1000 support beads of any one type are extracted, for example, not more than 500 support beads, not more than 300 support beads, or not more than 200 support beads of any one type are extracted.

According to various embodiments, in the case where multiple supports are collected of each type of oligonucleotide support, adjusting or varying the number of support beads dispensed relative to a reference number of support beads can compensate for support bead variation and normalize ultimate oligonucleotide concentration during use. This can be particularly advantageous when a standard deviation is large, for example, greater than 5% or greater than 10%. According to various embodiments, storage and retrieval robot 100 can quantify oligonucleotide concentration for individual Support beads, or batches of support beads. According to various embodiments, storage and retrieval robot 100 or associated equipment can take a sample subset of a group of support beads, and empirically measure the actual oligonucleotide amount contained on or in the support beads. For example, a sample subset of group of support beads can be subjected to a mass spectroscopy measurement to determine the quantity of oligonucleotide or other material present on or in each support bead. According to various embodiments, an empirical quantification can be used to establish a normalization ratio or other adjustment factor, to adjust the number of support beads for normalization and dispensing. According to various embodiments, for example, if a reference number of sample support beads is 100, then those 100 support beads collected from one oligonucleotide container can provide a reference amount and/or concentration of oligonucleotides in a pooling tube or in a mixture retainment region. If the quantification measurement, for example, a mass spectrometer measurement, for a particular oligonucleotide indicates a different than expected oligonucleotide amount per support bead, then the storage and retrieval robot 100 can adjust or normalize collection operations to extract more or less than the nominal reference support bead number, to compensate for those variations.

For example, in the case of a lower than expected oligonucleotide amount per support bead, the storage and retrieval robot 100 can adjust or normalize the collection to more than the reference support bead number. For example, if the oligonucleotide support beads are empirically measured to contain 99.0% of an intended reference amount, then the search and retrieval robot 100 can collect 101 support beads instead of 100 support beads. Conversely, if the empirical measurement for a particular set of oligonucleotide support beads indicates a greater than expected oligonucleotide amount per support bead, then the storage and retrieval robot 100 can adjust or normalize the collection to fewer than the reference support bead number. For example, if an oligonucleotide concentration measures at 111.1% of an intended reference amount, the storage and retrieval robot 100 can adjust or normalize the collection of support beads to 90 support beads, instead of 100. Other ratios, adjustments, and normalizing factors or amounts can be used. According to various embodiments, therefore, when a support bead pool is collected and the extracted oligonucleotides are cleaved into solution, the amount of each oligonucleotide in the pool can be corrected to be present at the same or at a desired amount or concentration.

According to various embodiments, the ability of storage and retrieval robot 100 to collect and dispense a selective number of multiple different types of support beads provides an advantage of averaging out potential variation in the number of oligonucleotides or other material on a particular support bead or group of support beads. For example, each support bead can vary in size, chemistry, porosity, loading, and other physical, chemical, or other, parameters. These variations can result in a different number of oligonucleotides on each support bead of a group of support beads. If only one support bead were to be collected, this expected variation can directly result in a variation in oligonucleotide concentration in solution. In the case, however, where multiple support beads are collected and dispensed, those variations can be averaged over the number of support beads, statistically reducing the variation and minimizing the effects of standard deviation, or of a known deviation, for a target value.

Other embodiments of the present teachings will be apparent to those skilled in the art from consideration of the present specification and practice of the teachings disclosed herein. It is intended that the present specification and examples be considered as exemplary only.

What is claimed is:

1. A system comprising:
    at least one retainment region, each retainment region of the at least one retainment region being adapted to retain a respective supply of support beads, each support bead comprising one or more reagents supported thereby, each reagent having a respective concentration with respect to each respective support bead;
    at least one mixture retainment region;
    at least one capture device, wherein the at least one capture device comprises a vacuum device and a movable piston in a housing; and
    a control unit programmed to control the at least one capture device to extract a calculated plurality of support beads from one or more regions of the at least one retainment region, wherein the calculated plurality of support beads is extracted from the at least one retainment region by setting the movable piston with respect to the housing to admit the calculated plurality into the housing under vacuum force supplied by the vacuum device and to control the dispensing of the extracted calculated plurality of support beads into the at least one mixture retainment region.

2. The system of claim 1, wherein the at least one retainment region comprises a plurality of retainment regions, and each of the plurality of retainment regions contains a respective supply of support beads.

3. The system of claim 2, wherein each of the respective supplies of support beads is different that one or more of the other supplies of support beads.

4. The system of claim 2, wherein at least two different supplies of support beads comprise one or more of the same reagents.

5. The system of claim 2, wherein the plurality of retainment regions comprises an addressable array of retainment regions.

6. The system of claim 5, wherein the control unit is programmed to control the at least one capture device to access a plurality of retainment regions of the addressable array.

7. The system of claim 6, wherein access to each retainment region is provided by movement of the at least one capture device.

8. The system of claim 6, wherein the control unit is adapted to receive a plurality of addresses corresponding to two or more retainment regions of the addressable array, and transfer one or more pluralities of support beads from two or more of the plurality of retainment regions to the at least one mixture retainment region.

9. The system of claim 2, wherein at least one of the supplies of support beads comprises support beads comprising an oligonucleotide reagent.

10. The system of claim 1, wherein the calculated plurality comprises an integral number of support beads.

11. The system of claim 1, wherein the vacuum device and movable piston operate under control of the control unit.

12. A method of handling support beads comprising oligonucleotides, the method comprising:
    providing at least one capture device, wherein the capture device comprises a vacuum device and a movable piston in a housing; said capture device adapted to be programmably positioned adjacent to at least one retainment region, each of the at least one retainment regions being adapted to retain a respective supply of support beads, each support bead of each respective supply comprising a concentration of a reagent supported thereby; and
    controlling the at least one capture device to extract a calculated plurality of support beads from a respective one of the at least one supply, wherein the calculated plurality of support beads is extracted from the at least one retainment region by setting the movable piston with respect to the housing to admit the calculated plurality into the housing under vacuum force supplied by the vacuum device and to dispense the extracted calculated plurality of support beads into at least one mixture retainment region.

13. The method of claim 12, wherein the at least one retainment region comprises a machine readable identifier and the method further comprises causing a machine to read the machine readable identifier.

14. The method of claim 12, wherein the controlling comprises receiving support bead content data, and the method further comprises adjusting the quantity of support beads extracted from the respective one of the at least one supply.

15. The method of claim 14, wherein the received support bead content data comprises information pertaining to a concentration of oligonucleotide supported by the respective support beads.

16. The method of claim 15, wherein the information pertaining to a concentration of oligonucleotide is determined by measuring oligonucleotide concentration using mass spectroscopy.

17. The method of claim 16, wherein the adjusting comprises increasing or decreasing the quantity of support beads extracted to achieve a normalized amount of reagent.

18. The method of claim 17, further comprising forming a solution comprising the reagent, wherein the normalized amount comprises an amount substantially equal to an amount expected to provide a nominal concentration of the reagent in the solution.

19. The method of claim 18, wherein the reagent comprises an oligonucleotide.

20. The system of claim 1, wherein the calculated plurality has been determined based on the concentrations of the one or more reagents supported by the support beads of the respective supply of support beads.

21. The method of claim 12, wherein the calculated plurality is determined based on the concentration.

* * * * *